United States Patent
Catto

(10) Patent No.: US 8,768,464 B2
(45) Date of Patent: Jul. 1, 2014

(54) PROGRAMMER FOR CARDIAC IMPLANTABLE MEDICAL DEVICES, HAVING AN ACCELERATED TEST MODE OF THE PARAMETERS

(75) Inventor: Giovanni Catto, Gentilly (FR)

(73) Assignee: Sorin CRM S.A.S., Clamart Cedex (FR)

( * ) Notice: Subject to any disclaimer, the term of this patent is extended or adjusted under 35 U.S.C. 154(b) by 1385 days.

(21) Appl. No.: 12/106,413

(22) Filed: Apr. 21, 2008

(65) Prior Publication Data

US 2008/0262561 A1    Oct. 23, 2008

(30) Foreign Application Priority Data

Apr. 19, 2007    (FR) ...................................... 07 02826

(51) Int. Cl.
*A61N 1/00* (2006.01)
(52) U.S. Cl.
USPC ............................................. 607/27; 607/30
(58) Field of Classification Search
USPC ................................................ 607/27, 59, 60
See application file for complete search history.

(56) References Cited

U.S. PATENT DOCUMENTS

| | | |
|---|---|---|
| 5,833,623 A | 11/1998 | Mann et al. |
| 6,487,451 B1 | 11/2002 | Casset et al. |
| 6,618,622 B1 | 9/2003 | Mann et al. |
| 6,907,290 B2 | 6/2005 | Legay |
| 7,003,349 B1 * | 2/2006 | Andersson et al. ............. 607/27 |
| 2004/0143304 A1 | 7/2004 | Hall et al. |
| 2007/0156188 A1 | 7/2007 | Casset |

\* cited by examiner

*Primary Examiner* — Eric D. Bertram
(74) *Attorney, Agent, or Firm* — Foley & Lardner LLP

(57) ABSTRACT

A programmer for cardiac implantable medical devices, including an accelerated test mode of the operating parameters. The programmer includes a user interface (10) that is used to define the tests to be performed on the implant and display the results thereof. These tests includes: ventricular and atrial sensing sensitivity, ventricular and atrial lead impedance, and ventricular and atrial capture threshold. Each test step involves (i) a predetermined setting of the operating mode, pacing rate and atrio-ventricular delay of the implantable device, (ii) collection of the operating data of the implantable device according said predetermined settings, and (iii) processing and display of thus collected data. There further exists one test step of time compression along which at least some of the ventricular and atrial tests for a same parameter are executed simultaneously during a common step, preferably the tests of sensing sensitivity and lead impedance. The user interface allows for a preliminary selection of the tests to be performed, and the programmer is operated to execute these tests, linked in sequence, without any intervention by the user.

20 Claims, 2 Drawing Sheets

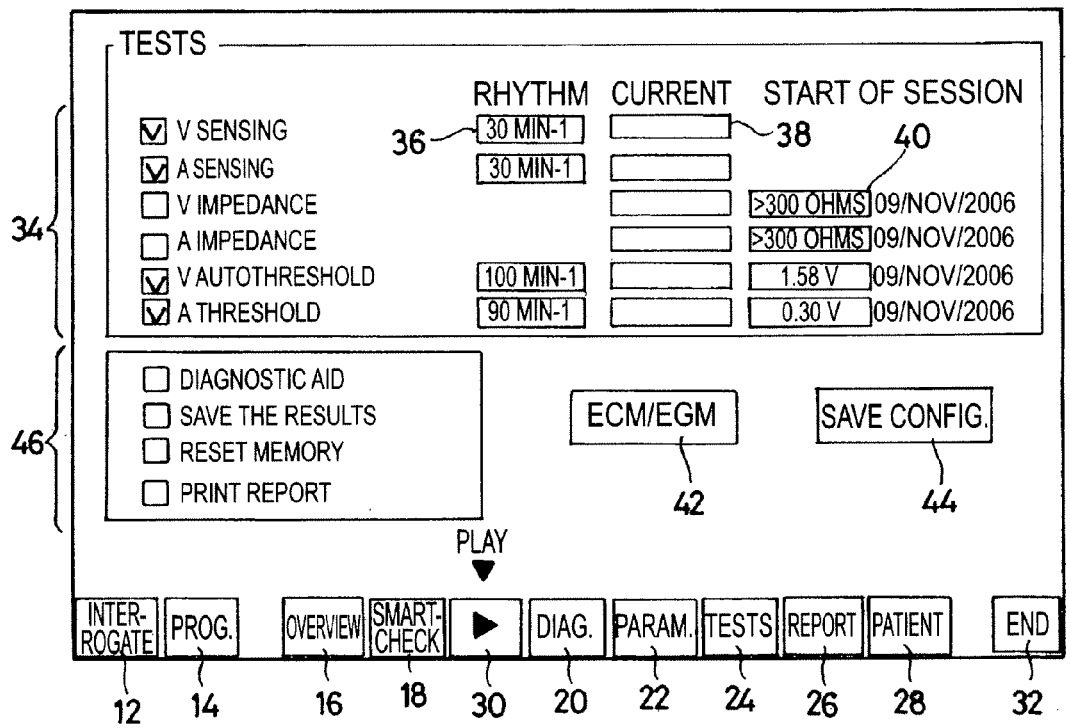
FIG_1
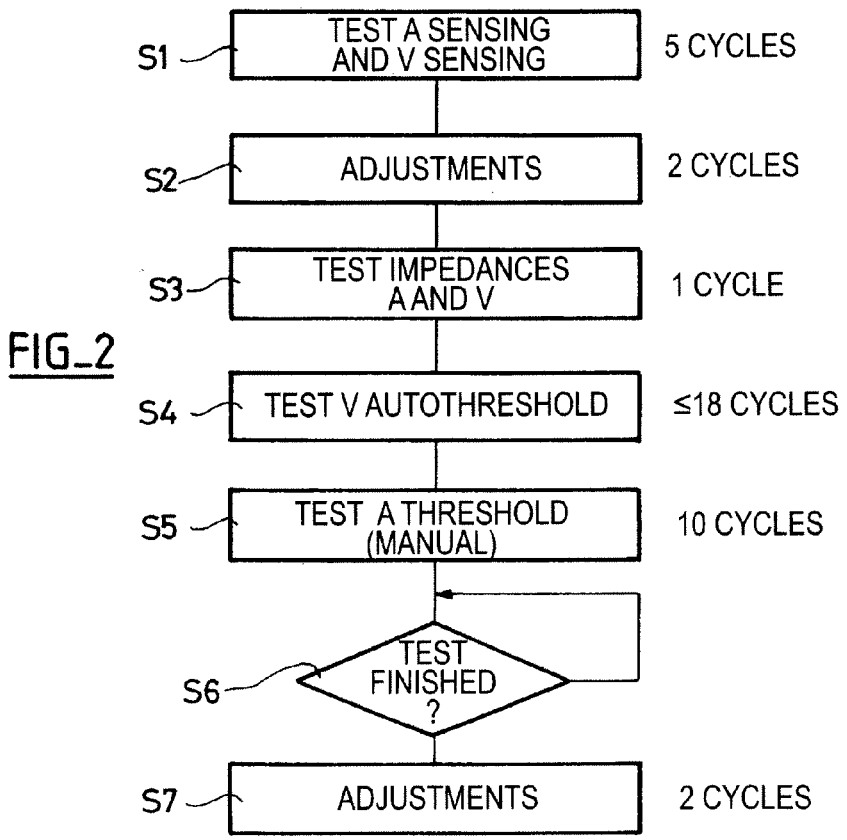
FIG_2

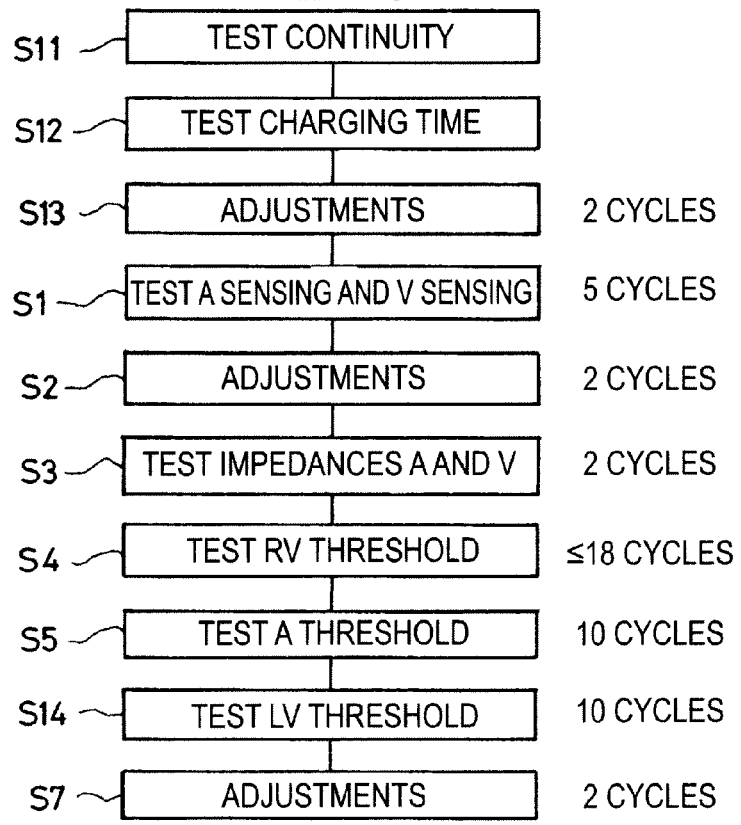
FIG_3
FIG_4

PROGRAMMER FOR CARDIAC IMPLANTABLE MEDICAL DEVICES, HAVING AN ACCELERATED TEST MODE OF THE PARAMETERS

FIELD OF THE INVENTION

The present invention is related to external programmers intended to be used with "active implantable medical devices", as such devices are defined by the Jun. 20, 1990 directive 90/385/CEE of the Council of the European Communities, and more particularly to those external programmers for use with implantable cardiac pacing, resynchronization, cardioversion and/or defibrillation devices.

BACKGROUND OF THE INVENTION

The programmer allows a practitioner to interrogate the implantable device and read the contents of its memories, and to program the implantable device so as to modify its settings or drive the execution of various algorithms, to provide software updates, to operate tests, etc.

Once the implantable device is positioned in a patient, and its leads connected, it is necessary to verify that a plurality of parameters are properly set at the moment of the implantation procedure, and thereafter on a regular basis or from time to time during follow-up visits.

The main parameters to be tested are: sensing sensitivity, lead impedance and capture threshold. These tests are typically performed for both the atrium and ventricle. In the case of a defibrillator, the test also covers the continuity of the shock coil or electrode, and the charging time for the shock capacitor to reach its nominal energy value. Finally, for multi-site devices, notably the implantable devices for cardiac resynchronization therapy ("CRT"), it is also necessary to test the parameters relating to the left ventricle (impedance of the coronary lead for left ventricular pacing, and capture threshold of left ventricular electrode). Performance of these tests is typically controlled by the practitioner, through the programmer.

U.S. Pat. Nos. 7,003,349, 6,618,622 and 5,833,623 describe some devices adapted to the execution of such tests. The practitioner can notably use and create "scripts" that define a sequence of operations through which the different requested tests are automatically linked to perform in sequence, one after the other.

When the practitioner schedules performance of one test, it results in putting the implanted device in a particular operating mode (DDI, DOO, etc.), with a particular pacing rate (the value being either chosen by the practitioner or set by the programmer to a default value) and a particular AV delay. The programmer then collects the operating data of the implanted device with such predetermined settings, and displays on a screen the result of the test thus performed. These tests can be practically launched by pressing a button available to the practitioner (e.g., an actual physical button, or a clickable zone on the screen), with each pressing of the button triggering the corresponding test.

The time required for executing the various tests is a major issue. In the first place, it is highly desirable to shorten the testing phase, for it constitutes a preliminary step to any interpretation or diagnosis, and therefore a dead time throughout the duration of the visit to the practitioner. Furthermore, from the patient's viewpoint, during the tests the implanted device is adjusted with test-specific predetermined settings, and its operation is not that for which it is normally parameterized. The implanted device is therefore not adapted to the patient's physiology throughout the duration required for these tests to be performed. It is therefore highly desirable, for a safety purpose, to abbreviate as much as possible this phase of tests.

OBJECTS AND SUMMARY OF THE INVENTION

It is, therefore, an object of the present invention to reduce the duration required for executing the various tests of the implanted device operation.

Advantageously, one skilled in the art will observe that, in accordance with the present invention, the total duration of the implanted device tests can be reduced to less than one minute, whereas in the known practice, this duration is never shorter than 2 min 15 sec or 2 min 30 sec. This reduction in time is significant.

It is yet another object of the present invention to propose to the practitioner the execution of specific actions that are automatically linked to perform in sequence, one after the other, the execution of the test steps, without any need for the operator's intervention, including, but not limited to: memorization (saving to memory) of results, print-out of a report, activation of a diagnosis-aid module, etc.

Broadly, the present invention is directed to operating a temporal compression of the test sequence by automatic performance of the different tests, with overlap (simultaneous execution) of some of them.

One aspect of the invention is directed to a programmer that, in a manner that is already known per se in the prior art (see, for example, U.S. Pat. No. 7,003,349), comprises a telemetry system for a bidirectional coupling with the implant, and a user interface, for defining the tests to be performed on the implant and displaying the results of these tests. These tests comprise at least part of the tests selected from among the following group: ventricular sensing sensitivity, atrial sensing sensitivity, ventricular lead impedance, atrial lead impedance, ventricular capture threshold, atrial capture threshold. The programmer also comprises command means for executing a plurality of test steps, each step comprising (i) a predetermined setting of the operation mode, pacing rate and atrio-ventricular delay of the implanted device, (ii) collecting the implanted device operating data as a function of said predetermined settings, and (iii) processing and display of the data thus collected.

In a manner characteristic of the present invention, the plurality of test steps comprises at least one step of time compression, along which at least some of the ventricular and atrial tests of a same parameter are executed simultaneously during a common step. The term "simultaneously" as used herein means that the concerned tests are concomitant, and they are: executed in parallel over a same time interval, in contrast to an execution that would be performed "successively" or "alternately" or "sequentially".

According to another characteristic of this invention, the user interface comprises means for preliminary selection by the user of the tests to be performed, and the command means is able to link in a sequence, without any intervention by the user, the execution of the corresponding selected test steps.

According to various particular embodiments of this invention, the command means is preferably able to execute at least one step of adjustment, interpositioned between two test steps implying a change of the pacing mode and/or rate of the implanted device, and/or a step of adjustment of the pacing mode and/or rate and/or atrioventricular delay of the implanted device, after execution of the last test step.

The command means is preferably able to command the execution of at least the following: one simultaneous test of atrial and ventricular sensing sensitivity, over $N_1$ cycles, preferably $N_1=5$ cycles; one simultaneous atrial and ventricular lead impedance test, over $N_2$ cycles, preferably $N_2=1$ cycle; one step of ventricular capture threshold, over $N_3$ cycles, preferably $N_3 \leq 18$ cycles; one step of atrial capture threshold, over $N_4$ cycles. Further, in a preferred embodiment, the step of the ventricular capture threshold test is executed over $N_3=N_3'+N_3''$ cycles, $N_3'$ being a fixed number of calibration cycles, and $N_3''$ a variable number of cycles of capture test with successive decreasing pulse amplitudes, the command means being able to terminate the ventricular capture threshold test as soon as a loss of capture is detected.

In yet another embodiment, the command means is also able to command the execution of at least the following: one step of continuity of the shock coil or shock electrode; a step of test of the charging time of the shock capacitor; and distinct steps of left and right ventricular capture threshold tests;

The user interface preferably comprises means for preliminary selection by the user of at least one specific action to be linked to perform in sequence, without any intervention by the user, after execution of the test steps. Notably, the actions are taken from among the group comprising: memorization of the test results in the implanted device memory, memorization of the test results in the programmer, print-out of the test results and activation of a diagnosis-aid module following the tests.

BRIEF DESCRIPTION OF THE DRAWINGS

Further features, advantages and characteristics of the present invention will become apparent to a person of ordinary skill in the art in view of the following detailed description of preferred embodiments of the invention, made with reference to the drawings annexed in which like reference characters refer to like elements, and in which:

FIG. 1 illustrates a first example of a display screen constituting the user interface of the programmer of this invention, for executing the tests of operation of a cardiac pacemaker;

FIG. 2 is a flowchart showing the linking of the different test steps likely to be scheduled by the practitioner by means of the user interface of FIG. 1;

FIG. 3 illustrates a second example of a display screen constituting the user interface of the programmer of this invention, for executing the tests of operation of a multisite device including features of resynchronization and/or defibrillation; and FIG. 4 is a flowchart showing the linking of the different test steps likely to be scheduled by the practitioner by means of the user interface of FIG. 3.

DETAILED DESCRIPTION OF THE INVENTION

One will now describe exemplary embodiments of a device according to the present invention.

Regarding the software aspects thereof, this invention can be implemented through an appropriate programming of the operating software of a known programmer. This invention can notably be applied to retrofit the REPLY and PARADYM brand programmers commercialized by ELA Medical, Montrouge, France, intended to program implantable devices such as SYNERGY and SYNDELI brand devices also commercialized by ELA Medical. These programmers are microcomputers specifically configured so as to implement the programming features, in conjunction with a telemetry head connected to the computer and coupled to the implantable device through inductive or radiofrequency (RF) communications protocols in a known manner.

Adapting these devices for implementing the features of this invention by software programs of the functions described herein is believed to be easily within the abilities of a person of ordinary skill in the art, and will therefore not be described in detail in this document. On FIG. 1, reference 10 illustrates the graphic user interface to be displayed to the practitioner on a programmer display screen. In a manner already known per se, this interface comprises an "interrogate" button 12 for commanding the interrogation of the memories and registries of the implanted device, and a program ("prog.") button 14 for programming the operating parameters thereof. The screen 10 further comprises a certain number of buttons 16, 18, 20, 22, 24, 26, 28 allowing to select respective functions including: viewing the implanted device status ("overview" 16), triggering of tests ("Smartcheck" 18), activation of a diagnosis-aid module ("Diag." 20), parameterization ("Param." 22), verification ("Tests" 24), report ("Report" 26), patient identification (Patient 28).

The button 18 for triggering the tests is associated with a "start" or "play" button 30, intended to execute, following the manner that is specific to this invention, the different tests of operation of the implanted device. An "end" button 32 allows to terminate the follow-up session.

The display screen comprises a certain number of checkboxes 34, allowing the practitioner to select the tests he/she wishes, or not, to execute: ventricular sensing sensitivity (V sensing), atrial sensing sensitivity (A Sensing), ventricular lead impedance (Impedance V), atrial lead impedance (Impedance A), ventricular capture threshold (V Autothreshold), which can be automatically determined by the implanted device, atrial capture threshold (A threshold), which is usually determined manually or "by hand", for it requires an interpretation of the data by the practitioner.

Regarding the sensing sensitivity tests and capture threshold tests, a field 36 shows the rate to which the pulse generator will be adjusted, the default value being possibly modifiable by the practitioner. The "current" fields 38 allow to display the respective test results after execution of these tests, and fields 40 show the results of the test previously performed by the implant, e.g., at the start of the session, for this same parameter, with the corresponding date. Indeed, the values of certain parameters, notably the impedance and the capture threshold, are automatically measured by the implant in an autonomous manner, and at regular intervals (for example, every 5 hours). These are the values that are displayed in the fields 40.

A button 42 allows to review a posteriori the electrocardiogram (ECG) and electrogram (EGM) associated to the execution of these tests, and a "Save Config." button 44 allows to store in a memory of the programmer, the results of these tests (the memorization of test results in the implant being subjected to another command).

The interface 10 also comprises a certain number of checkboxes 46 allowing the practitioner to command the execution of specific actions by the programmer, immediately after the achievement of the test sequence: activation of a diagnosis-aid module, saving the test results in the implant memory, reset of this memory, print-out of a report.

The sequence of the different tests is represented in the flow-chart of FIG. 2. The illustrated sequence corresponds to the execution of the totality of the tests that are possibly selectable through checkboxes 34, but should some of these boxes be not checked, the corresponding steps would of course be omitted or skipped during the running of the whole sequence.

The first step S1 consists of evaluating the atrial and ventricular sensing sensitivities. These two measurements are performed simultaneously along this single step S1. Typically, the settings of the implanted device are: DDI mode, AV delay of 250 ms, default pacing rate of 30 bpm (or any other value programmed by the practitioner). This step can be performed in only 5 cycles, corresponding to a duration of 10 seconds at a pacing rate of 30 bpm.

The following step S2 is a step of adjustment allowing to compensate the modifications of the operating mode, AV delay and pacing rate between the step S1 and following step S3. In this step of adjustment S2, the settings of the implant become: DOO mode, programmed AV delay, pacing rate of 100 bpm. The typical duration is 2 cycles.

The following step S3 is a step of measurement of the ventricular and atrial lead impedances. With the settings of the previous step S2 (DOO mode, programmed AV delay, 100-bpm pacing rate), this test can be performed in only one cycle, simultaneously for ventricular and atrial electrodes. It is notably possible to implement a technique for lead impedance measurement that is described in U.S. Pat. No. 6,907,290 (commonly assigned herewith to ELA Medical).

The following step S4 is a step of determination of the ventricular capture threshold. The settings of the implanted device are: DOO mode, AV delay of 94 ms, default pacing rate of 100 bpm (or any other value programmed by the practitioner). This step S4 is composed of a first phase of calibration, typically over 7 cycles, followed by a step of capture threshold test with decreasing pulse amplitudes. In a preferred embodiment, the test is considered completed when a loss of capture is detected, that allows to shorten the duration of this step. The maximum duration of this step S4 is preferably 18 cycles (with the least favorable assumption when the loss of capture is not detected, or only detected in the last cycle). It is notably possible to implement a technique of adjustment of the pacing pulse amplitude that is described in U.S. Pat. No. 6,487,451 (commonly assigned herewith to ELA Medical), with a phase of calibration followed by a phase of search for a loss of capture.

The following step S5 is a step of measurement of atrial capture threshold. Though there are existing techniques for automatic measurement of this threshold, such as that described in US published patent application US 2007/0,156,188 (commonly assigned herewith to ELA Medical), it may be preferable, for safety reasons, to rely upon an actual interpretation performed manually by the practitioner.

To that end, the pulse generator is driven over 10 cycles with the following settings: DAO mode, AV delay of 250 ms, default 100-bpm pacing rate (or any other value programmed by the practitioner). At the end of these tests, the practitioner indicates (step S6) the value of the atrial capture threshold based upon his/her interpretation of the cardiac signals that have been displayed on an intermediate screen.

When these different tests have been completed, the sequence ends with two cycles of adjustment, as shown in step S7, so as to put the pulse generator back in its original configuration, as it was prior to the tests.

One will observe that the steps of adjustment S2 and S7 are required so as to allow an automatic linking of all the successive steps, which differs from prior known configurations in which the tests were commanded one after the other by the practitioner, for example, through successive clicks on a button. Such tests were executed individually, interpreted visually, and the settings determined for each of the tests, every time, without any consideration for the settings of the previous test. On the contrary, in accordance with the present invention, the settings for a given test are dependent upon those used for the previous test, and for this reason, for example, in order to link the tests S1 of sensing sensitivity and S3 of impedance, it is necessary to have an intermediate step of compensation S2 in order to realize the change of operating mode (from DDI to DOO in this example) and pacing rate (from 30 bpm to 100 bpm in this example) in a totally automatic manner.

With the numbers of cycles and pacing rates described above, one can reach an overall duration of approximately 45 seconds at the most for steps S1-S5 and S7 (the duration of the ventricular capture threshold test can usually be reduced, as explained above). If it is assumed that the average duration for step S6 of interpretation of the atrial capture threshold test and selection of the threshold value by the practitioner is about 10 seconds, one gets an overall duration for steps S1-S7, of 55 seconds at the most—to be compared to usual durations of 2 min 15 sec to 2 min 30 sec with a manual test sequence.

FIG. 3 illustrates the interface that is displayed to the practitioner for the test of a multisite device including features of resynchronization and/or defibrillation/cardioversion, in accordance with an alternate embodiment of the present inventions.

This interface similarly comprises the checkboxes 34' present in the interface of FIG. 1, as well as additional parameters to be tested, notably including (as a function of the type of implanted device): left ventricular lead impedance ("LV impedance"), continuity of shock coil (so-called "supraventricular" electrode and/or distal ventricular electrode) ("SV continuity"), charging time of the shock capacitor to its nominal energy ("charging time 34J"), left ventricular capture threshold ("LV threshold"), eventually right ventricular capture threshold in manual mode ("RV threshold") (to test manually, by comparing them, the capture thresholds for the two ventricular cavities), and test of optimization of a resynchronization therapy ("CRT optimization").

The remaining information presented on the screen are the same as those referred to in FIG. 1.

FIG. 4 is a flowchart that illustrates the linking of the different selected test steps. In additional to the steps S1 to S7 as described above with respect to FIG. 2 (step S6 is not shown in FIG. 4), the sequence comprises the following additional steps:

step S11 for the test of continuity of the defibrillation coil(s), step S12 for the charging time test, step S13 for adjustment (two cycles) to restore the pulse generator to its programmed values for operating mode, AV delay, pacing rate and amplitude, step S14 for left ventricular capture threshold (LV threshold), with following parameters: DAO mode, AV delay of 94 ms, default 100-bpm pacing rate (or any other value programmed by the practitioner). The total duration of this step S14 is of 10 cycles.

Here again, the automatic linking of the different steps, and the temporal overlap of the atrial and ventricular tests, allow a significant gain in reducing the test duration in accordance with the present invention as compared to the usual sequence of the known prior art.

One skilled in the art will appreciate that the present invention can be practiced by other than the described embodiments and particular values referenced for the various operating and programmable parameters, which are presented for purposes of illustration and not of limitation.

I claim:

1. A programmer for an active implantable medical device of the type for pacing, resynchronization, cardioversion or defibrillation of the heart, said programmer comprising:
   telemetry means for establishing a bidirectional coupling of said programmer with the active implantable medical device;
   a user interface, for defining a first set of tests to be performed on the active implantable medical device, and displaying the results of said tests, said first set of tests including at least one selected from among the group consisting of: ventricular sensing sensitivity, atrial sensing sensitivity, ventricular lead impedance, atrial lead impedance, ventricular capture threshold, and atrial capture threshold; and
   command means for executing a plurality of test steps, each step comprising (i) a predetermined adjustment of the settings of said active implantable medical device comprising at least one of an operating mode, a pacing rate and an atrioventricular delay, (ii) collection of the active implantable medical device operating data following said predetermined adjusted settings, and (iii) processing and display of the data thus collected,
   wherein said plurality of test steps comprises said first set of tests including at least one step of time compression along which at least some of the atrial and ventricular tests for a same parameter are performed simultaneously, in a non-sequential manner, during a common single step.

2. The programmer of claim 1, wherein the user interface comprises means for preliminary selection by the user of the tests to be performed, and said command means further comprising means for linking in a sequence, without any intervention by the user, the execution of one or more of the corresponding test steps.

3. The programmer of claim 1, wherein said command means further comprises means for executing at least one adjustment step interpositioned between two test steps, applying a change of operating mode and/or pacing frequency of the active implantable medical device.

4. The programmer of claim 1, wherein said command means further comprises means for executing at least one step of adjustment of the operating mode, the pacing rate and the atrio-ventricular delay of the active implantable medical device after execution of the last test step.

5. The programmer of claim 1, wherein said command means further comprises means for commanding the execution of at least each of the following:
   one step of simultaneous test of ventricular and atrial sensing sensitivities, over $N_1$ cycles, one step of simultaneous test of atrial and ventricular lead impedances, over $N_2$ cycles, one step of ventricular capture threshold test, over $N_3$ cycles, one step of atrial capture threshold test, over $N_4$ cycles.

6. The programmer of claim 5, wherein said step of simultaneous test of ventricular and atrial sensing sensitivities is executed over $N_1=5$ cycles.

7. The programmer of claim 5, wherein said step of simultaneous test of atrial and ventricular lead impedances is executed over $N_2=1$ cycle.

8. The programmer of claim 5, wherein said step of ventricular capture threshold test is executed over $N_3=N_{3'}+N_{3''}$ cycles, $N_{3'}$ being a predetermined fixed number of calibration cycles and $N_{3''}$ being a variable number of capture test cycles with successive pulses of decreasing amplitude, said command means being able to terminate the ventricular capture threshold test when a loss of capture is detected.

9. The programmer of claim 8, wherein $N_3 \leq 18$ cycles.

10. The programmer of claim 1, wherein said command means further comprises means for commanding the execution of at least each of the following:
    one step of continuity test of the shock coil, one step of test of charging time of a shock capacitor, and distinct steps of right and left ventricular capture threshold test.

11. The programmer of claim 1, wherein said user interface comprises means for preliminary selection by the user of at least one specific action to be linked in sequence, without any further intervention by the user, after the execution of said test steps.

12. The programmer of claim 11, wherein said at least one specific action further comprises an action selected from among the group consisting of: memorization of the test results in the active implantable medical device, memorization of the test results in the programmer, print out of the test results, and activation of a diagnosis-aid module following the tests.

13. A method of testing an implantable medical device, the method comprising:
    determining, at a programming device, a set of tests to be performed on the implantable medical device, wherein the set of tests comprises tests configured to sense one or more of the following parameters: ventricular sensing sensitivity, atrial sensing sensitivity, ventricular lead impedance, atrial lead impedance, ventricular capture threshold, and atrial capture threshold;
    for each test of the set of tests:
       transmitting, from a programming device to the implantable medical device, instructions configured to cause the implantable medical device to perform the test, wherein the instructions are configured to cause the implantable medical device to adjust one or more settings of the implantable medical device to conduct the test; and
       receiving, at the programming device, operating data from the implantable medical device following adjustment of the one or more settings;
    wherein the instructions are configured to cause the implantable medical device to perform at least a portion of an atrial test and a ventricular test for at least one of the parameters simultaneously, in a non-sequential manner.

14. The method of claim 13, wherein determining the set of tests to be performed comprises receiving input from a user interface identifying the set of tests to be performed.

15. The method of claim 13, wherein the instructions are configured to cause the implantable medical device to perform at least a portion of the set of tests in a sequential manner.

16. The method of claim 13, further comprising transmitting results based on the operating data to a display device for display to a user.

17. A method of testing an implantable medical device, the method comprising:
    receiving, at the implantable medical device, instructions from a programming device;
    performing, at the implantable medical device, a set of tests in response to receiving the instructions, wherein the set of tests comprises tests configured to sense one or more of the following parameters: ventricular sensing sensitivity, atrial sensing sensitivity, ventricular lead impedance, atrial lead impedance, ventricular capture threshold, and atrial capture threshold, wherein, for each of the set of tests, performing the test comprises:
       adjusting one or more settings of the implantable medical device; and transmitting operating data of the implantable medical device from the implantable medical device to the programming device following adjustment of the one or more settings;

wherein performing the set of tests comprises performing at least a portion of an atrial test and a ventricular test for at least one of the parameters simultaneously, in a non-sequential manner.

18. The method of claim 17, wherein the set of tests performed is determined based on input from a user interface identifying the set of tests to be performed.

19. The method of claim 17, performing the set of tests further comprises performing at least a portion of the set of tests in a sequential manner.

20. The method of claim 17, further comprising transmitting the operating data to a display device for display to a user.

* * * * *